(12) United States Patent
Sevdermish

(10) Patent No.: US 8,046,274 B2
(45) Date of Patent: Oct. 25, 2011

(54) METHOD FOR DIGITAL COLOR GRADING OF GEMS AND COMMUNICATION THEREOF

(76) Inventor: Menahem Sevdermish, Herzila (IL)

( * ) Notice: Subject to any disclaimer, the term of this patent is extended or adjusted under 35 U.S.C. 154(b) by 1087 days.

(21) Appl. No.: 11/070,266

(22) Filed: Mar. 3, 2005

(65) Prior Publication Data

US 2005/0149369 A1 Jul. 7, 2005

Related U.S. Application Data

(63) Continuation-in-part of application No. 10/470,740, filed as application No. PCT/IL02/01057 on Dec. 31, 2002, now abandoned.

(60) Provisional application No. 60/350,926, filed on Jan. 25, 2002.

(51) Int. Cl.
*G06Q 30/00* (2006.01)
*G06Q 10/00* (2006.01)

(52) U.S. Cl. .................. 705/27.1; 705/306

(58) Field of Classification Search .......... 705/306, 705/27.1, 27.2, 28, 29, 37, 35; 356/243.5, 356/402, 421, 30, 425; 707/999.001, 999.01, 707/999.1, 999.102; 434/386, 96; 702/1, 702/81; 382/100
See application file for complete search history.

(56) References Cited

U.S. PATENT DOCUMENTS

| | | | |
|---|---|---|---|
| 5,828,405 A | 10/1998 | Vanier et al. | |
| 5,950,178 A * | 9/1999 | Borgato | 705/37 |
| 5,966,673 A | 10/1999 | Shannon | |
| 5,983,238 A | 11/1999 | Becker et al. | |
| 6,020,954 A | 2/2000 | Aggarwal | |
| 6,239,867 B1 | 5/2001 | Aggarwal | |
| 6,304,853 B1 | 10/2001 | Malnekoff | |
| 6,381,510 B1 | 4/2002 | Amidhozour et al. | |
| 2001/0024532 A1 | 9/2001 | Malnekoff | |
| 2002/0021439 A1 | 2/2002 | Priestley et al. | |
| 2002/0052170 A1 | 5/2002 | Holloway | |
| 2003/0065586 A1 * | 4/2003 | Shaftel et al. | 705/27 |
| 2003/0115079 A1 | 6/2003 | Rapaport | |
| 2004/0030565 A1 * | 2/2004 | Hendry Jr | 705/1 |

(Continued)

FOREIGN PATENT DOCUMENTS

GB 2159636 4/1985

(Continued)

OTHER PUBLICATIONS

??? "OctoNus: Diamond Calculator", Print-Out From the Internet:Dec. 2000.

(Continued)

*Primary Examiner* — Igor Borissov

(57) ABSTRACT

A method of color grading gems by a user by their inherent properties of shape, hue, tone and saturation. Each of the properties is variable over a practical range derived from a database. The database is created by digitally coding gem shapes, hues, tones and colors from digital photographs of gems of different, shapes, hues, tones and saturation. The variable properties are displayed on a screen and the user selects the best matching respective shape, hue, tone and saturation in comparison to the particular gem being graded. Upon receiving the user's selections, an image of the a gem having the shape, hue, tone and saturation selected by the user is displayed on the screen and translated into alpha-numeric code which can be communicated to any other user of the same system, enabling remote discussion and evaluation of the same target gem.

5 Claims, 9 Drawing Sheets

U.S. PATENT DOCUMENTS

| | | | |
|---|---|---|---|
| 2004/0068417 | A1 | 4/2004 | Sevdermish |
| 2004/0072137 | A1* | 4/2004 | Lapa et al. .................. 434/386 |
| 2005/0149369 | A1 | 7/2005 | Sevdermish |

FOREIGN PATENT DOCUMENTS

| | | |
|---|---|---|
| GB | 2159636 | 12/1985 |
| GB | 2358541 | 7/2001 |
| JP | 02-128564 | 5/1990 |
| JP | 03-017076 | 2/1991 |
| JP | 2000-020681 | 1/2000 |
| JP | 2001-201454 | 7/2001 |
| WO | WO 86/04991 | 8/1986 |
| WO | WO 93/12496 | 6/1993 |
| WO | WO 01/91011 | 11/2001 |
| WO | WO 03/062942 | 7/2003 |

OTHER PUBLICATIONS

International Search Report Dated Oct. 1, 2004 From the International Searching Authority Re.: Application No. PCT/IL02/01057.
Official Action Dated Jun. 13, 2008 From the Japanese Patent Office Re.: Application No. 2003-562739 (Translation Only).
Official Action Dated Jun. 23, 2004 From the US Patent Office Re.: U.S. Appl. No. 10/470,740.
Official Action Dated Oct. 28, 2004 From the US Patent Office Re.: U.S. Appl. No. 10/470,740.
Official Communication Dated Sep. 4, 2008 From the European Patent Office Re.: Application No. 02806572.0.
Official Communication Dated Oct. 26, 2007 From the European Patent Office Re.: Application No. 02806572.0.
Supplementary European Search Report Dated Mar. 10, 2005 and Received Mar. 28, 2005 From the European Patent Office Re.: Application No. EP 02806572.0.
OctoNus "OctoNus: Diamond Calculator", Print-Out From the Internet:Dec. 2000.
Communication Pursuant to Article 94(3) EPC Dated Jul. 29, 2009 From the European Patent Office Re.: Application No. 02806572.0.
Office Action Dated Nov. 1, 2009 From the Israel Patent Office Re.: Application No. 163201 and Its Translation Into English.
Office Action Dated Apr. 2, 2009 From the Israeli Patent Office Re.: Application No. 163201 and Its Translation Into English.
Response Dated Jan. 5, 2010 to Communication Pursuant to Article 94(3) EPC of Jul. 29, 2009 From the European Patent Office Re.: Application No. 02806572.0.
Response Dated Mar. 10, 2010 to Office Action Dated Nov. 1, 2009 From the Israel Patent Office Re.: Application No. 163201.
Translation of Notice of Reason for Rejection Dated Apr. 17, 2009 From the Japanese Patent Office Re.: Application No. 2003-562739.
Brinn "Israeli Software Program Powers International Gem Color System", ISRAEL21c Newsletter, Oct. 15, 2006.
Gia "GIA Says It Will Use Gemewizard Software in Its Colored Stone Courses (Facets)", The Gemological Institute of America (GIA), HighBeam™ Research, A Part of the Gale Group, Inc., 2009.
Translation of Official Decision for Rejection and Dismissal of Amendment Dated Mar. 12, 2010 From the Japanese Patent Office Re.: Application No. 2003-562739.
Office Action Dated Jun. 27, 2010 From the Israel Patent Office Re.: Application No. 163201 and Its Translation Into English.
Translation of Notice of Reason for Rejection Dated Jun. 13, 2008 From the Japanese Patent Office Re.: Application No. 2003-562739.
Decision to Refuse a European Patent Application Dated May 26, 2011 From the European Patent Office Re.: Application No. 02806572.0.
Communication Pursuant to Article 94(3) EPC Dated Sep. 4, 2008 From the European Patent Office Re.: Application No. 02806572.0.
Communication Pursuant to Article 96(2) EPC Dated Oct. 26, 2007 From the European Patent Office Re.: Application No. 02806572.0.
Response Dated May 5, 2011 to Summons to Attend Oral Proceedings Pursuant to Rule 115(1) EPC of Mar. 3, 2011 From the European Patent Office Re. Application No. 02806572.0.
Summons to Attend Oral Proceedings Pursuant to Rule 115(1) EPC Dated Mar. 3, 2011 From the European Patent Office Re. Application No. 02806572.0.
Response Dated Oct. 26, 2010 to Office Action of Jun. 27, 2010 From the Israel Patent Office Re.: Application No. 163201.

* cited by examiner

METHOD FOR DIGITAL COLOR GRADING OF GEMS AND COMMUNICATION THEREOF

RELATED APPLICATIONS

The present application is a continuation-in-part of U.S. patent application Ser. No. 10/470,740, filed Aug. 11, 2003 now abandoned, which is a National Phase of PCT patent application No. PCT/IL02/01057, filed Dec. 31, 2002, which claims priority from U.S. Provisional Application No. 60/350,926, filed Jan. 25, 2002, now expired.

FIELD AND BACKGROUND OF THE INVENTION

The present invention relates to a computer based grading system of gems, including the method of construction of a database serving the said system. The method is particularly useful for communication of grading results over the phone or Web, when the parties discussing the results rely on the image of the target gem as displayed by the system.

A major problem facing the gem dealer, grader and jeweler is how to accurately assess and grade consistently the color of a given gem, what descriptive language to use and how to communicate the color of gems over the fast and growing Internet or, for that matter, over the phone.

The color gamut of gems is vast, including thousands of color possibilities. Using the present methods for color communication used today, which are briefly described below, one finds it difficult or practically impossible to communicate and describe the accurate color (hue, saturation and tone) of a certain gem.

Sending the actual images of a large number of gems is time consuming due to the limitations of the speed of transfer of data. Even if such a transfer would be faster in the future one is still left with the problem of grading the gems according to accepted grades of colors, which are well defined and known.

Existing systems for color grading of gems, are for example:

The Gemset (GIA Gem Instrument, the Gemological Institute of America, Carlsbad, Calif.). This is a method of determining the color grade of gems by comparing the color of a gem to be graded, with plastic molds representing round shapes of various hues, tones and saturations. Each sample is labeled with the GIA nomenclature. The Gemset has several drawbacks:

1. Comparing real gems to plastic samples is difficult due to the different look, texture, brilliance and sparkle of plastic and real gems.
2. The presence of only rounds samples may affect the quality of grading when comparing them to gems of other shapes.
3. Limited amount of samples of colors, (324) as not all colors are present.
4. Some colors have to be interpolated or estimated by the grader or examiner, (tone and saturation) causing inconsistency of the results, especially when the same gem is examined by several experts.
5. Difficulty to find the right sample to compare with the real gem.
6. The fading of the colors of the plastic samples after a while.
7. No record of the gem grading is left after the process.
8. One can communicate the results of the grade over the phone or Internet, only if the receiving party a) has the Gemset b) can pick the same color sample, and c) reach the same conclusion as the examiner.

Advantages of the Gemset method: an accepted nomenclature by the trade.

The Gemdialogue: consists of flat, transparent acetate sheets having 10 zones of saturation levels (from 10% to 100%) in 44 spectral hues and an additional sheet of acetate having tone grade from black to transparent.

Draw backs are obvious, and all the above drawbacks apply. In addition to these:

a) Too much speculation is left to the grader.
b) The grades and nomenclature used to describe the color are not easy to communicate, say P2B70/30 which means moderate purplish blue, zone 70 (70% saturation) with the 30% black mask overlay.
c) One finds it difficult to visualize the color of the described gem.

The Munsell Book of Color (Macbeth div. of Kollmorgen Instruments Corp. New Windsor, N.Y.). An elaborated system used to determine colors, using 1600 flat, glossy, opaque, printed chip samples in 40 pages each representing a certain hue Drawbacks are as above. This method is not suitable for grading gems.

The Inventor is the author of a 2-volume book related to gems, titled "The Dealers Book of Gems and Diamonds", 1997. These books deal with gemology and commercial aspects of gems trading and processing.

The following patents, for example, cover the issue of gem evaluation, grading and reporting, but none covers the invention henceforth described: U.S. Pat. Nos. 5,899,503; 4,291,975; 6,239,867; 5,966,673; 5,615,005; 4,534,644; 4,527,895; 4,461,568.

Other patents cover the field of color selection, for example: U.S. Pat. No. 5,103,407 (Gabor). Color selection methods are practiced by computer methods running on color screens, for example: the color selection method offered by Microsoft Windows for non-standard colors available for their "desk top" opening screen.

BRIEF SUMMARY OF THE PRESENT INVENTION

According to one aspect of the present invention, there is provided apparatus for color grading a particular gem, comprising: a database having stored therein images of a number of different gem shapes, various hues for each gem shape, various tones for each hue, and various saturations for each hue; a screen including a field for displaying a composite image of a selected gem shape having a selected hue of a selected tone and a selected saturation; and a dataprocessor programmed: a) to enable a user to select from the database a gem shape best matching the shape of the gem to be graded; b) to enable the user to select from the database a particular hue, a particular tone, and a particular saturation best matching the hue, tone and saturation of the gem to be graded; c) to display in said field of the screen a composite image of a gem having the shape, hue, tone and saturation selected by the user; and d) to identify the gem shape, the hue, the tone, and the saturation selected by the user from said date base for display in the field of the screen, to thereby enable the user to produce a precise definition of the shape, hue, tone and saturation of the composite image displayed, and thereby of the particular gem being graded, and to communicate the precise definition to another.

According to a further feature in the described preferred embodiment, the dataprocessor is programmed to identify the gem shape, the hue, the tone, and the saturation in the displayed image by a string of alphanumeric code elements including a first code element identifying the gem shape, a second code element identifying the hue, a third code element identifying the tone, and a fourth code element identifying the saturation in the image displayed in the first mentioned field.

In one described preferred embodiment, the particular gem to be graded is displayed in a further field located proximately to the first mentioned field in which the gem shape, hue, tone and saturation selected from the database are displayed, to facilitate a visual comparison between the displays in the two fields for making the best match selections. In another described preferred embodiment, the particular gem to be graded is itself visually inspected by the user and visually compared with the gem shapes, hues, tones and saturations stored in the database when making the best matched selections.

According to further features in the described preferred embodiments, the screen includes a further field identifying the different gem shapes in the database; and the dataprocessor is programmed to enable the user to select from the further field of the screen the gem shape in the database best matching the shape of the gem to be graded and to be displayed in the first mentioned field. Preferably, the screen includes still further fields identifying the various hues, tones and saturations in the database; and the dataprocessor is programmed to enable the user to select from the still further fields of the screen the hue, tone and saturation in the database best matching the hue, tone and saturation of the gem to be graded and to be displayed in the first mentioned field.

According to yet another aspect of the present invention, there is provided a method of creating a database particularly useful for color grading gems, comprising: digitally coding a number of different gem shapes, and assigning a first code element to each such shape; digitally coding a number of different hues for each gem shape, and assigning a second code element to each such hue; digitally coding a number of different tones for each hue, and assigning a third code element to each such tone; digitally coding a number of different saturations for each tone, and assigning a fourth code element to each such saturation; and storing the digitally coded gem shapes, hues, tones and saturations in a manner to permit each of the shapes, hues, tones and saturations to be selectively accessed by their respective code elements, and to be displayed as an image on a computer screen.

In the described preferred embodiments, the gem shapes, hues, tones and saturations are digitally coded from 2-D digital photographs of a large number of gems of the different shapes, hues, tones and saturations.

The present invention thus enables gems to be graded by using a personal computer having a storage device, for example; a hard disc, an operating system, a color calibrated screen, an Internet browser and Web communication means. An expert pre-prepared database of gem 3D cuttings and ranges of color gamut, represented by hue-tone-saturation combinations, reside in the storage device.

As will be described more particularly below, this expert database is compiled on the basis of a real collection of thousands of gems representing commercial shapes (cuts) and colors, digitally converted into the coherent groups ("rulers") on which the novel grading method is based.

In the described preferred embodiment, the method of gem grading is interactive, by which the user is comparing a target gem to be evaluated, which is presented on the computer color screen, to an image of a synthetic gem of the same cut which is gradually built-up by the user in hue, tone and saturation to visually match the target gem. For this process the user is directed by the novel method to use groups of colored images, imitating the cut of the target gem, in a relevant gamut of hues, and finally to variants of hue-tone and saturation, which progressively close the visual gap between the target gem and the final image representing the grading result. The user's choice in the comparison process, as well as the final best visual match, is translated by the computer to an alphanumeric code representing hue-tone-saturation-cut variables. This code is the "language" communicated between users (graders, experts, traders) of the invented system. Keying the same code in far apart systems, having identical built-in databases, will display the same gem, in aspect of hue-tone-saturation and cut, on the screen.

The code can be linked to other gem relevant databases, either residing in the storage means of the user's computer or available on the Web. Such databases can be, for example, price, stock or availability listings.

In another embodiment of the invention the same grading method can be adapted to specific characteristics of certain gem groups or diamonds. In this embodiment more features related to the gem to be graded can be entered into consideration, for example, size, weight or clarity.

BRIEF DESCRIPTION OF THE DRAWINGS

The invention is herein described, by way of example only, with reference to the accompanying drawings, wherein:

FIG. 3 and FIG. 4 schematically illustrate two auxiliary tone-saturation tables used to explain the structure of the secondary display of 45 hue-tone-saturation combinations of FIG. 5.

FIG. 12 schematically illustrates the Diamond Details window, part of the Diamond Mode, shown in FIG. 11.

FIG. 13 schematically illustrates the CutWizard, a linked expert tool attached, for example, to the Diamond Details window shown in FIG. 12.

DESCRIPTION OF A PREFERRED EMBODIMENT

Figure 1A:
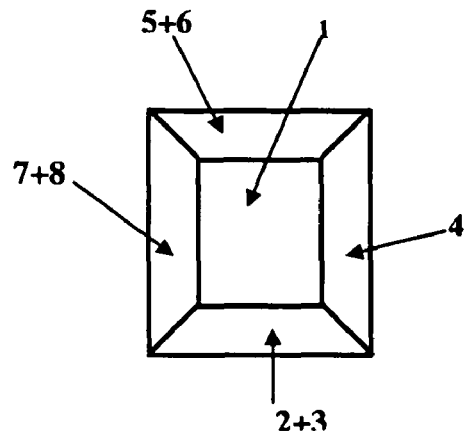
FIGS. 1A and 1B schematically illustrate one phase in the creation of the master shape 3D ruler.

The invention runs on the known in the art personal computer (PC), having exemplary characteristics:

Personal Computer: Pentium II, or better.

A free memory of 200 MB on its hard disc.

Microsoft Windows 95 Operating System, Office 97 or above

Microsoft or Netscape browser

Monitor—A 800/1000 resolution and higher

As will be described more particularly below, the foregoing computer components are arranged to define apparatus for color grading a particular gem in accordance with the present invention. Briefly, such apparatus comprises: a database having stored therein data representing a number of different gem shapes, various hues for each gem shape, various tones for each hue, and various saturations for each hue; a screen including a field for displaying a composite image of a selected gem shape having a selected hue of a selected tone and a selected saturation; and a dataprocessor programmed to perform a number of functions, including the following:

a) to enable a user to select from the database a gem shape best matching the shape of the gem to be graded;

b) to enable the user to select from the database a particular hue, a particular tone, and a particular saturation best matching the hue, tone and saturation of the gem to be graded;

c) to display in said field of the screen an image of a gem having the shape, hue, tone and saturation selected; and d) to identify the gem shape, the hue, the tone, and the saturation selected for display in the field of the screen, to thereby enable the user to produce a precise definition of the shape, hue, tone and saturation of the particular gem being graded, and to communicate the precise definition to another.

Glossary:

The following professional expressions will be used throughout the description of the preferred embodiment:

a) Color components: the color is composed of three main components:

Hue—the dominant and any additional colors visible in a color. For example: greenish blue.

Saturation—the purity or the intensity of the hue of the color.

Tone—the lightness or darkness (from colorless to black) of the color.

When one reduces the saturation of a color, in a given gem, the gem loses hue and turns either brownish or grayish, however when you reduce the tone of a color in a given hue, the gem displays a lighter color of the same hue.

b) GIA, the Gemological Institute of America: A non profit organization, considered to be the most important gemological institute in the world, world class educational center and an authority in gems, diamonds and gemology.

The source of much of the nomenclature and grading systems of diamonds and gems used today.

The Database:

The preferred embodiment of the invention required the one-time creation of a digital database of images of facetted gems of practically all possible colors, enabling the display of these images in all shapes and types of gem cutting.

The following method was used for the creation of the database relying on images of real gems. Several thousands of real gems of a variety of colors (hues, tones and saturation) were professionally and digitally photographed, their images numbered, color graded by an expert, and computer stored. These gems were of all shapes and sizes. The same gems were kept as reference for later visual inspection under controlled lighting.

The Creation of the Master Shape 3D Ruler:

15 most popular shapes of cuttings were chosen to be included in the master. These were: round, emerald cut, oval, trillion, pear-shape, heart shape, square, square princess, baguette, round cabochon, pear cabochon, oval cabochon and marquise cabochon.

Using a known in the art 3D program the facets of each and every shape, were drawn in 3D on the computer. Each facet accurately placed, representing the average looks, angles and proportion of these particular shapes in gems.

These images were stored in the computer as colorless images.

Figure 1B:
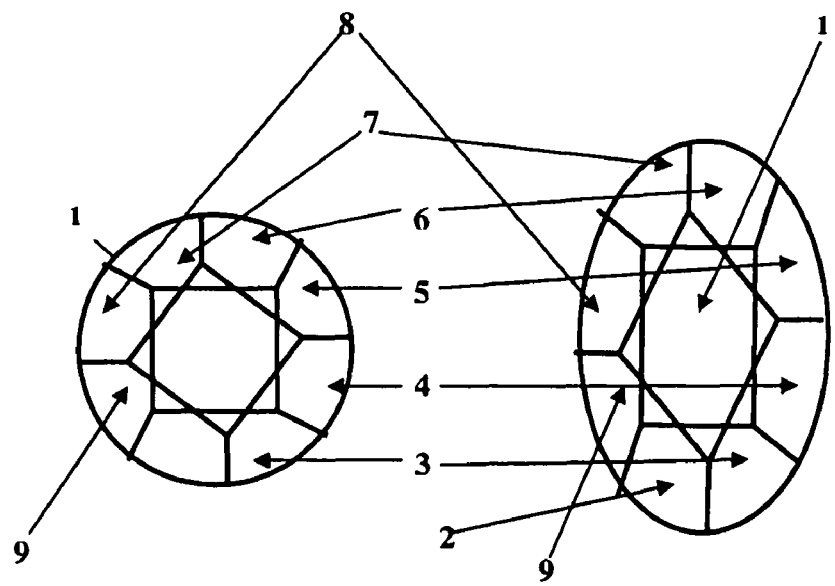

When all shapes were produced digitally, each facet of the gem was given a certain corresponding number—as shown in FIGS. 1A, 1B. For example the front facet will always be no. 1. The method of numbering guarantees that the number given to a certain facet of one shape represents a similar facet in another shape. Since the number of facets is not equal in all the shapes, and also the shape of each corresponding facet of the gem is not identical (for example: in emerald cut one finds elongated, rectangular facets of various sizes while in round shape many facets are triangular), in certain shapes, some of the corresponding "numbers" were eliminated or combined with others. This is demonstrated in FIG. 1A, while the method of "correspondence" of facets is two shapes shown in FIG. 1B.

Using the Adobe Photoshop program all these colorless shapes were laid side by side, in a certain order on one image named "master 3D ruler". The creation of the "master ruler" as described solves a major problem of finding gems of exactly the same colors in said 15 shapes. Such gems are practically impossible to find in nature. And even if found, their images would never be of identical color.

Also solved, was the problem of "natural look" that these digitally produced images of gems present, compared to gems which are drawn by designers, which rarely look natural.

Placing the Colors:

In order to produce a "ruler" having gems of identical looking colors in each of the shapes, facets of the same number in different shapes were pasted with the color of a facet of a natural gem image. This was done by marking the outline of each of the facets of the real gem image obtained, for example, by digital photography, "cutting and copying" them onto the corresponding facet in the 3D images. For example: "number 1" facets in the ruler would be pasted with that particular color of a "real" corresponding facet. Each facet reacts slightly differently when pasted in different facet outlines within the shapes, requiring some color corrections to be made. In such a way, the color of a round, real gem may result in becoming an oval shape or heart shape etc. in the "master 3D ruler".

Note: it must be emphasized that no sampling was done on the natural color, other than the actually copying of the "real" facet. This is important due to the fact that each facet has a certain texture of color and sparkle not evenly dispersed, and the relationship between the colors of each facet is of utmost importance to the overall look of the gem.

At the end of the process, a ruler having 15 images of gem shapes, each having practically equal color in comparison to its neighbor was created, having all images equal in color to that certain "real" gem color that they originated from.

This process was first done on the "crown" of the gems (the front part) and then repeated for the "pavilion" (back-side) of the gems.

The 36 Master Hue Rulers:

Once these digital images of the rulers were ready, 36 rulers, which represented the full scale of hues, were chosen out of over a thousand "original rulers".

This was done by comparing the color of a ruler to evenly graded hues within the full spectrum of visual colors as in known in the art image editing software programs such as Photoshop (Adobe, USA) and Photoimpression (by Arcsoft). The results were verified with Munsell Color Charts and the GIA Gemset used by the gem trade.

The chosen "master hue rulers" were numbered from 1 to 36, according to their position in an imaginary hue wheel. All those hues were of medium saturation of color and medium tone. The master hues are presented hereby in table 1.

Using the image editing software, each one of these master ruler hues was reduced and increased in tone and saturation, in measured steps (% of middle tone and saturation).

Six tone grades were chosen and numbered: (2) very very light (3) very light, (4) light, (5) medium, (6) dark and (7) very dark.

TABLE 1

| | |
|---|---|
| Blue | C1 |
| V. sl. greenish blue | C2 |
| sl. Greenish blue | C3 |
| greenish blue | C4 |
| Str. Greenish blue | C5 |
| V. str. greenish blue | C6 |
| green blue | C7 |
| V. str. bluish green | C8 |
| bluish green | C9 |
| V. sl. bluish green | C10 |
| green | C11 |
| V. sl. yellowish green | C12 |
| Sl. yellowish green | C13 |
| yellowish green | C14 |
| Str. yellowish green | C15 |
| yellow green | C16 |
| greenish yellow | C17 |
| yellow | C18 |
| orangy yellow | C19 |
| yellowish orange | C20 |
| Orange | C21 |
| reddish orange | C22 |
| orange red | C23 |
| orangy red | C24 |
| Red | C25 |
| sl. purplish red | C26 |
| str. Purplish red | C27 |
| purple red | C28 |
| reddish purple | C29 |
| Purple | C30 |
| bluish purpose | C31 |
| Violet | C32 |
| bluish violet | C33 |
| violet blue | C34 |
| Str. violetish blue | C35 |
| violetish blue | C36 |

Six saturation grades were chosen and numbered: (1) very lightly saturated, (2) lightly saturated, (3) moderately saturated, (4) saturated, (5) highly saturated and (6) vivid.

The steps (increase or decrease) were not linear and were not constant for all grades. Due to the nature of color, some hues tend to disappear when reduced in tone or saturation. For example yellow hues are practically undetectable to the naked eye when reduced in saturation by 80% while red or blue hues will be quite visible.

These newly created rulers were computer filed in each step, having their exact hue number, tone and saturation grade noted. This process created practically the full scale of colors possible for each of the 36 master hues.

The 1296 Master Rulers

The definition of 6 tone grades and 6 saturation grades resulted in 36 possibilities for each hue×36 master hues=1296 Master rulers.

Each of these rulers was corrected whenever certain details were lost or defused in the process. Each of these rulers was given a certain number, which stemmed from the original number of the master hue. Each of these rulers was adapted to the 15 chosen master shapes (each shape given a certain no from 1 to 15) creating a well organized collection of 19,440 files of gems of specific shapes, having a predetermined color.

To facilitate communication each of the 19,440 files can be numbered by the following method: first the master hue number (1 to 36), then the tone number (1 to 6), the saturation number (1 to 6) and the shape number (1 to 15). For example:

C1-7-5-2 refers to master hue blue (C1)—very dark (7) tone—highly saturated (5)—oval (2) shape (or cut). while C22-5-6-3 refers to reddish orange (C22), of medium tone (5), vivid saturation (6) and round shape (3).

Figure 2:
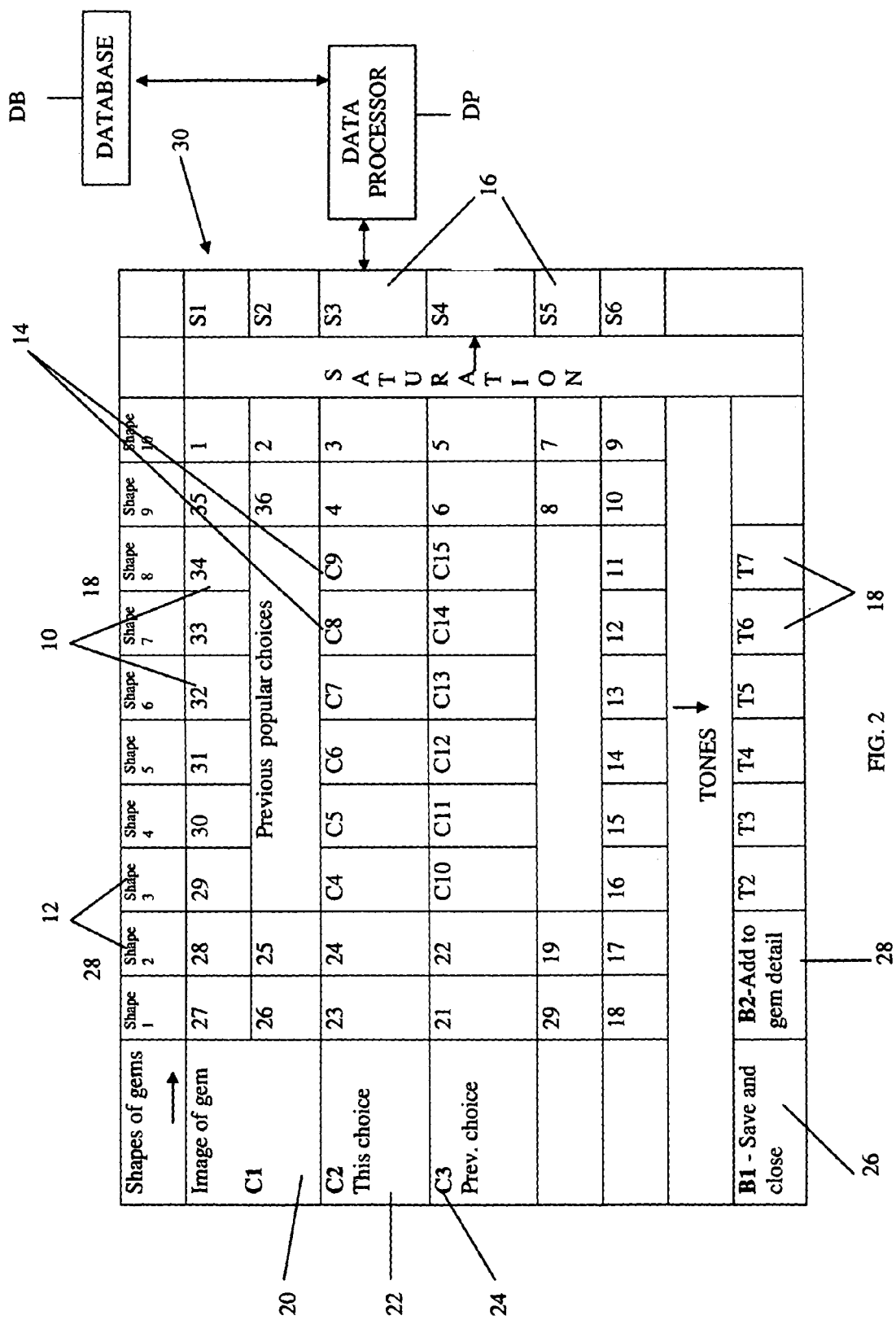
FIG. 2 schematically illustrates the main computer components of one form of apparatus constructed in accordance with the invention, particularly the color screen of the universal gem grading mode, including the 36 master hues.

The organization of the shape-hue-tone-saturation rulers into a coherent method, which enables gem grading, is shown in FIG. 2.

FIG. 2 presents a computer color screen 30, part of a computer system schematically shown as also including a database DB as briefly described above, and a data processor DP programmed to perform a number of operations, as briefly described above and as to be more particularly described below. The main screen 30 displays in its center part, the colors of the 36 basic hues 10, arranged in an orderly logical order. This is a substantially rectangular frame form, the horizontal rows being single and the vertical being double rows. These master hues are displayed in one singular default shape, namely "round".

The master shape ruler 12 displays the outlines of the most popular shapes (only 10 shapes) available in the system. Two side rulers are present, one displaying tone 18 marked T2-T7, and the other saturation 16 marked S1-S6.

Other available display fields are:

C1 field 20—for the imported image of the examined gem. This can be a digitally photographed image, or a high quality scanned image usually stored first in the computer's memory.

C2 field 22—for the present image, as composed in the method of grading to be explained further on.

C3 field—for the previous choice 24.

C4 to C15 fields are previous, often chosen popular images, or the images of the most popular chosen colors.

B1, B2 are exemplary command keys 26, 28.

The Preferred Mode of Operation of the Grading Method

Step #A The user selects from the computer memory the image of the target gem he/she wishes to grade. This is done by activation of field "C1" on the screen 30.

Step #B: The user should first choose a specific shape 12, which conforms to the cut or shape of the target gem 20. This will cause the screen 30 to display all the master hues 10, tone levels 18 and saturation levels 16 in that specific shape (making it particularly easy for the user to compare the color on the screen, with the shape of the gem in question 20).

Step #C: Next, the user should choose and key on the specific hue 10 closest to the color of the target gem 20 to be graded. This will automatically open an additional (secondary) 45 color system, which assists the user in narrowing down the grading options. In addition, fields 18 of screen 30 of FIG. 2 will display tones T2 to T7 related to the chosen hue, as well as saturation levels S1 to S6 in fields 16, as will be further explained at a later stage.

It should be noted that every step performed, as well as every one of the next grading steps, results in the gradual buildup of a composite gem image in field 22 on screen 30. This enables the user to closely observe and compare his grading results with the target gem 20 in the neighboring field.

If no image is available for field 20 (step #A), one may also perform grading in the same method, by comparing the grading result in field 22, to a properly illuminated, actual gem held by the user.

The 45 Color "Secondary System" Mode of Operation

Figures 3, 4:
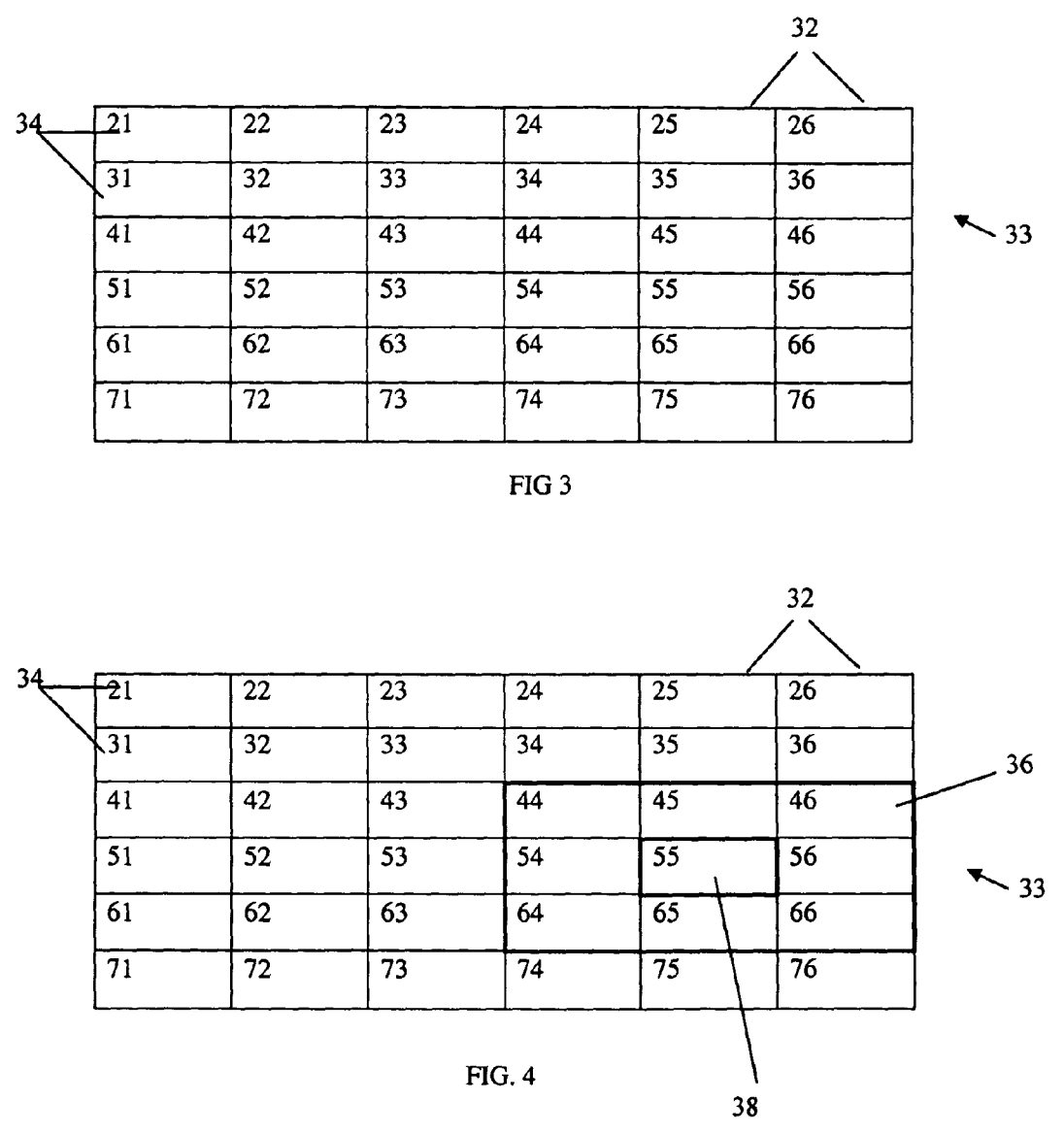

The "secondary system" is based on the structure of table 33 shown in FIG. 3, including the full combination of tone and saturation possibilities related to a chosen hue. The 36 fields of table 33 are numbered between "21" and "76", having the following significance:

The top row 32 represents tones which are all of the same tone level, namely 2 (very very light), having increasing (left to right) levels of saturation: "21", "22" . . . "26". The first number in the fields of this row relate to the tone level, while the second number stands for the (increasing) level of saturation.

The first column on the left 34 represents increasing (top to bottom) levels of tone with an equal, very low level of saturation (1), thus: "21", "31", "41" . . . "71".

The first number in the fields of this column relates to the tone level, while the second number stands for the (constant) level of saturation.

When a certain hue is chosen in step #C, say Number 18 of FIG. 2 (yellow), the system will open a new window (secondary display), which is based on table 33 over the center of screen 30 to display hues which are between 16 (yellow green), 17 greenish yellow, 18 (yellow), 19 orange yellow, and 20 yellowish orange (plus and minus 2 of the chosen "master" hue) altogether 5 hues. The structure of the "secondary display" will be explained herein in relation to FIG. 4.

It was noted before that all hues displayed on screen 30 of FIG. 2 are shown in their mid-range level tone/saturation, which can be interpreted in table 33 of FIG. 4 as field 38, having a tone/saturation level of (5). To enable a choice of alternatives around this mid-range level all the fields of tone/saturation surrounding the mid-range field 55 are chosen for the secondary display. These are the 9 tone/saturation levels 44, 45, 46, 54, 55, 56, 64, 65, 66 surrounded by the rectangle 36.

Figure 5:
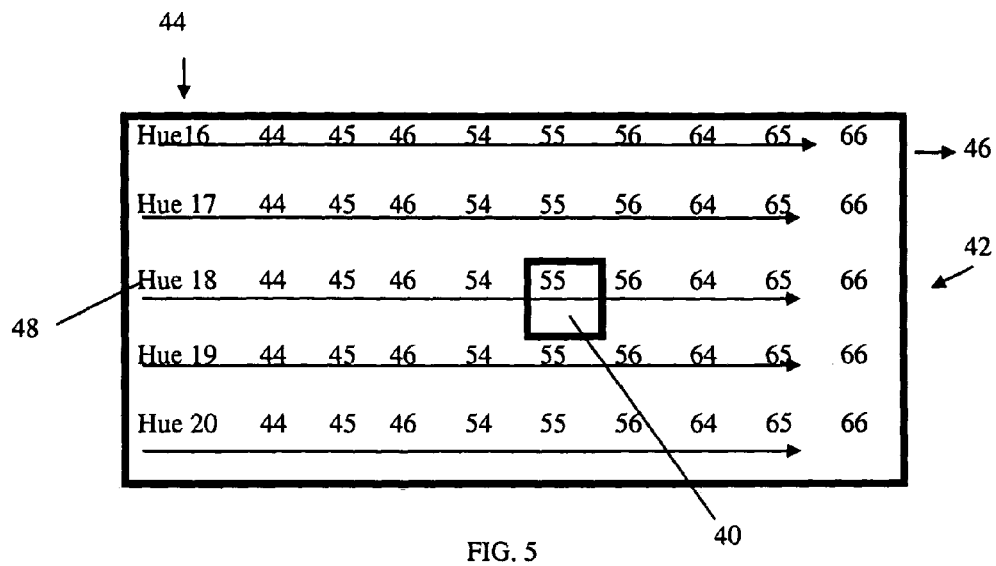
FIG. 5 schematically illustrates the secondary display of 45 hue-tone-saturation combinations related to the 36 master hues of FIG. 2.

The resulting "secondary display" is shown in FIG. 5, as an example, in which the user chose in step #C the hue yellow (no. 18). The table 42 includes 45 hue-tone-saturation combinations as follows: the vertical left column 44 defines 5 hues—plus minus 2 around the number of the hue chosen in step #C. In this example table 42 will show in the rows tone/saturation levels of the hues 16 (yellow green), 17 greenish yellow, 18 (yellow), 19 orange yellow, and 20 yellowish orange.

All the rows show tone/saturation levels 44, 45, 46, 54, 55, 56, 64, 65, 66 (progressing in direction 46) each row for the color indicated by the left column 44.

The "secondary display" (table 42) will be superimposed on screen 30 of FIG. 2 with field 40 highlighted to indicate the original choice of hue (yellow no. 18-5-5, in this example), permitting an additional consideration of 45 hue-tone-saturation combinations, each displayed in the shape/cut selected in step #B, on top of the single hue selected as first choice in step #C.

Step #D: the user refines his former hue selection by choosing the best fitting field in the "secondary display", which changes the hue-tone-saturation of the shape in field 22 of FIG. 2.

Step #E: in this step the user is able to consider more tone and saturation level, when comparing the two images in the adjacent fields 20 and 22 of FIG. 2, namely the target gem and the resultant image built up in steps #B to D.

Additional Tone-Saturation Options Related to the Chosen Hue.

Fields 16 (saturation levels) and 18 (tone levels) of FIG. 2 present more grading options of the chosen hue in steps #C, D.

Figure 6:
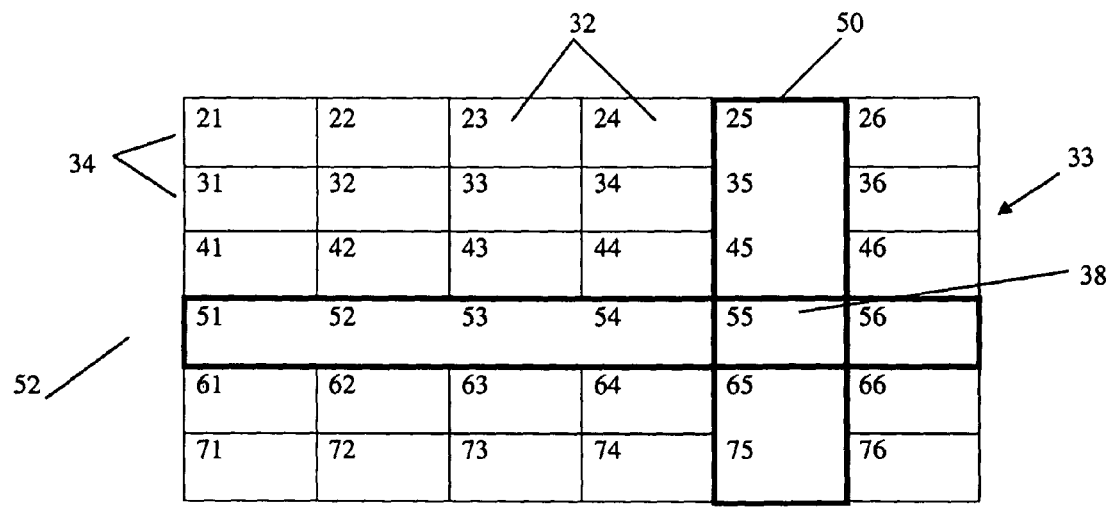
FIG. 6 schematically explains the display of the tone-saturation side rulers of FIG. 2.

Consider table 33 shown again in FIG. 6 with two highlighted rectangles: the two row—columns intersecting at the 5-5 level 38. The entire table here should be considered to be in the hue chosen, for example, in step #D. The row 52 will be represented in fields 16 of screen 30 as saturation variants 5-1, 5-2, 5-3, 5-4, 5-5, 5-6 (of the specific chosen hue) and column 50 will be represented in fields 18 as tone variants 2-5, 3-5, 4-5, 5-5, 6-5 (of the specific chosen hue).

The user can try in this step and choose one or more of these variants, which will result in each case in a parallel variation of the image in field 22.

Step #F: if the user feels that further refinement of his hue-tone-saturation choice done in steps#C, D, E, is needed because it is not accurate enough, he or she can initiate a third display (not shown) similar in structure of the "secondary display" with additional 45 grades, surrounding the hue chosen in step #D. The side rulers 16, 18 in the main screen 30 will change accordingly. This additional display assists the user in refining his decisions.

Display and Communication of the Final Grading Result

The final result is visually displayed in field C2 of FIG. 2 adjacent to the image of the real gem displayed in field C1. If more than one grading attempt is done, the previous choice is displayed in field C3.

The alphanumerical code, which represents the final step in the grading process, is recorded in an attached computer file. This file includes other details related to the gem as well as a verbal description of the resulting hue-tone-saturation-shape.

Assuming that the same grading steps are performed on various computers practicing the invented method, the same visual image will be displayed in field 22 and in the attached file. This feature of the invented method is of utmost importance to two or more experts situated in different places, while discussing the same actual gem.

The applications of the invented grading method and system stem from its basic features:

Color Communication

A user of the system wishes to discuss over the phone a certain gem color with another user, having the system installed on his or her computer. Communicating the same alpha-numeric code over the Internet, both users will be able to observe the same image on their computer display. During such a session many gem images can be displayed instantaneously instead of time consuming transfer of image files, as was done in the past.

Color Grading

The user is able to determine the color of the gem and grade it according to accepted standards. The grading results can be stored and retrieved at will.

Price Display

Being a computer system relevant data bases can be attached and linked, for example: price lists, inventory lists and availability lists. Updates can always be communicated over the Web to holders of the system by known in the art methods. When used for grading the system performs "immediate pricing" using all quality factors of gems and diamonds, when linked to files of pricelists which are available in the gem trade.

Any other data such as new colors of gems, and data about supply sources can be linked to images and grading results. To an extent, the system can be defined as a digital gem catalogue.

A Summary of Sample Applications of the System and Method:

The method enables the user to communicate shape, hue tone and saturation, by using a common visual language for the digitally produced colors of gems and to study the prices of particular colors of gems of various shapes.

Since the user's own personal computer acts as a server for images, grades and pricelists stored on the hard disc, it offers a very fast and accurate way to define, compare and grade the colors of gems.

The method covers a large data base of images (typically over 50,000 images) of digitally produced gems of various shapes and colors, all of which are accurately classified and positioned within a known gamut of hues, tone and saturation.

The nomenclature used for hues, tone and saturation correspond to internationally accepted grades by the GIA and the gem trade.

The user is able to choose a certain particular color from the system and search for that particular color in a range of gems, look for a match for a certain gem, or create sets of matching gems by searching through the data base for precise colors, shapes and qualities.

The system enables the user to keep a record of the chosen grade (image and grade) together with an image of the actual gem.

Colors displayed by the system depend only on the quality of the monitor used and the calibration of colors (which can be easily performed).

Practical Embodiments of the Invented Grading Method

Figure 7:
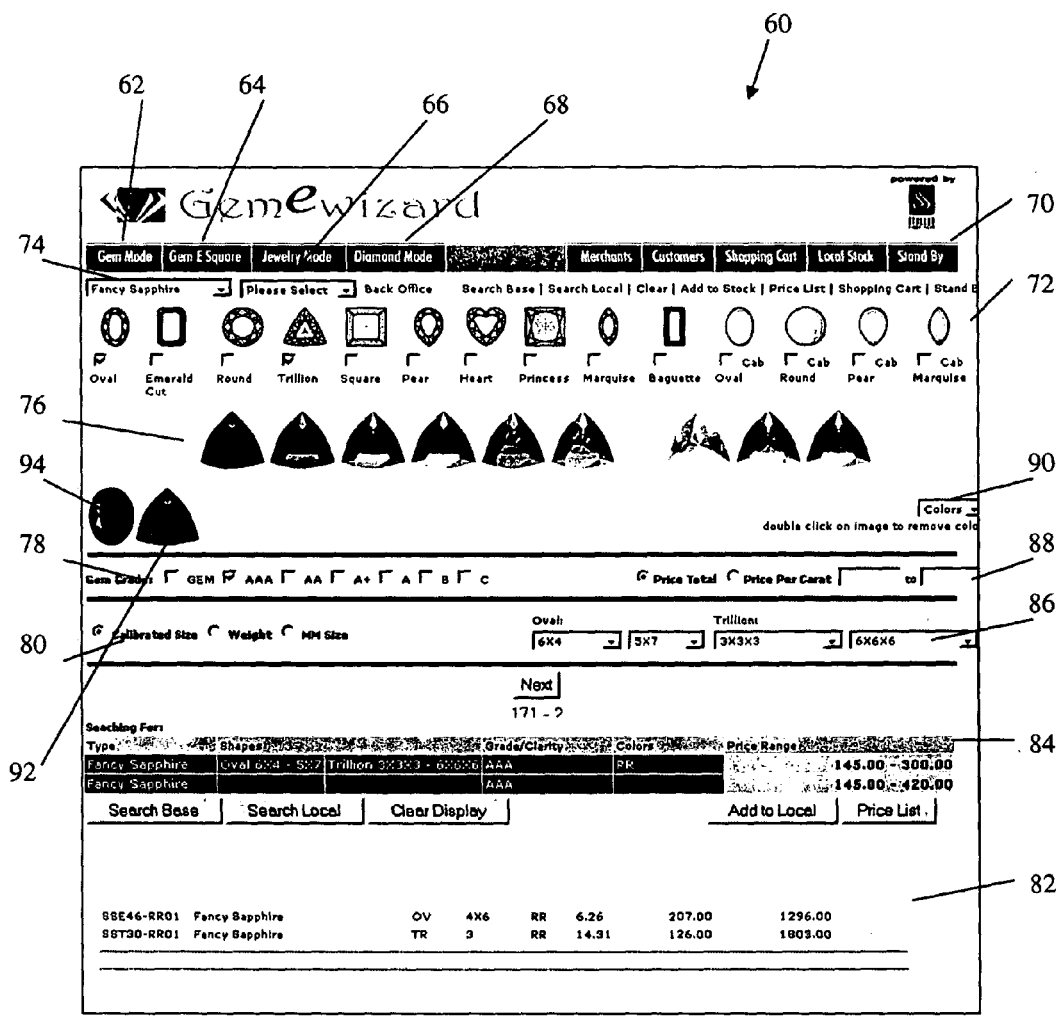
FIG. 7 schematically illustrates the main screen of the GemEwizard, a practical and commercial embodiment of the method of grading described in FIGS. 1 to 6.

FIG. 7 depicts the main screen 60 of the GemEwizard, a practical and commercial embodiment of the method of grading described in FIGS. 1 to 6.

The uppermost screen bar guides the user to the 4 possible modes of employment of this embodiment:
 a. Gem Mode 62
 b. GemESquare 64
 c. Jewelry mode 66
 d. Diamond Mode 68

The screen bar 72 guides the user to choose the gem form or cut, each with its commercial name (Oval, Emerald Cut, etc.).

Pull down window 74 lists available gem types by their commercial name (Fancy Sapphire, etc.).

The screen field 76 is employed during operation of the GemERuler tool for color selection. A sample GemERuler is shown in FIG. 7, and will be further discussed.

The screen bar 78 is for selecting gem grade, and screen bar 80 for measurements mode, calibrated sizes, weight in carat, size in mms.

The screen field 82 displays search results and 84—immediate pricing.

Pull down windows 86 are used for selecting size range (mms.) and 88 for selecting price range: total or per carat.

Pull down window 90 is used for selecting color/shape keys.

The operation of the GemEWizard will be further explained in some practical interactive grading methods.

The Gem Mode 62

The user is interested in the shape Trillion, selected on the screen bar 72

(FIG. 7). To define the required gem type pull down window 74 is used; in this example "Fancy Sapphire" is selected. The resulting screen display is shown in field 76: the GemERuler displays all popular colors of the gem type "Fancy Sapphire" in shape Trillion. Gem grades 78 can be further selected with the respective changes in the GemERuler display. This interactive selection mode enables the user to select the desired color, which is shown in position 92. If the user wants to examine the same color in Oval shape this is displayed next by position 94.

The system is able to perform the following tasks: a) color Grading, b) price determination, c) searching in inventory d) inventory control.

The GemESquare 64

Figure 8:
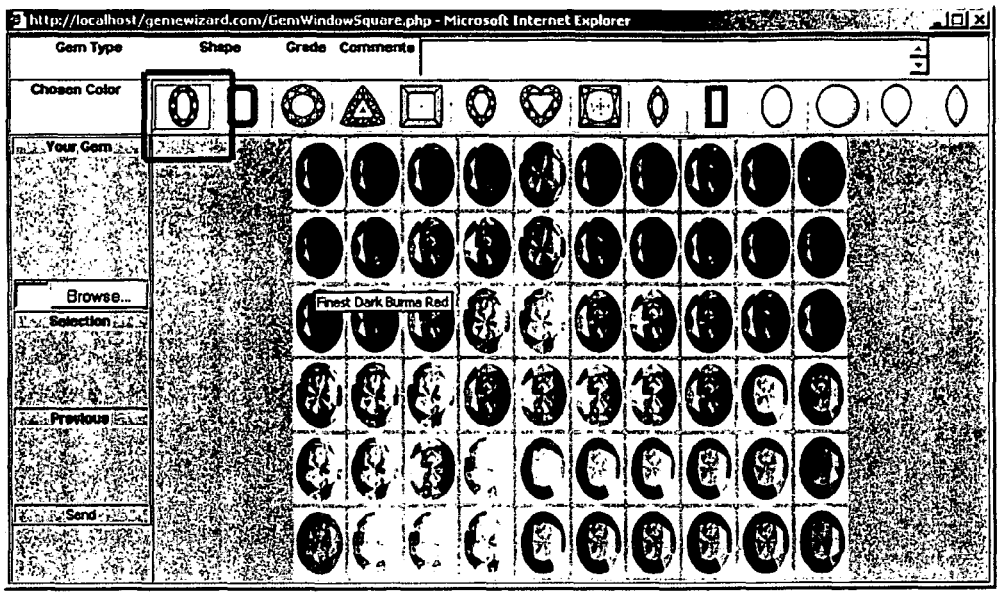
FIG. 8 schematically illustrates the 60 master hues of the GemESquare, one application included in the embodiment shown in FIG. 7.
Figure 9:
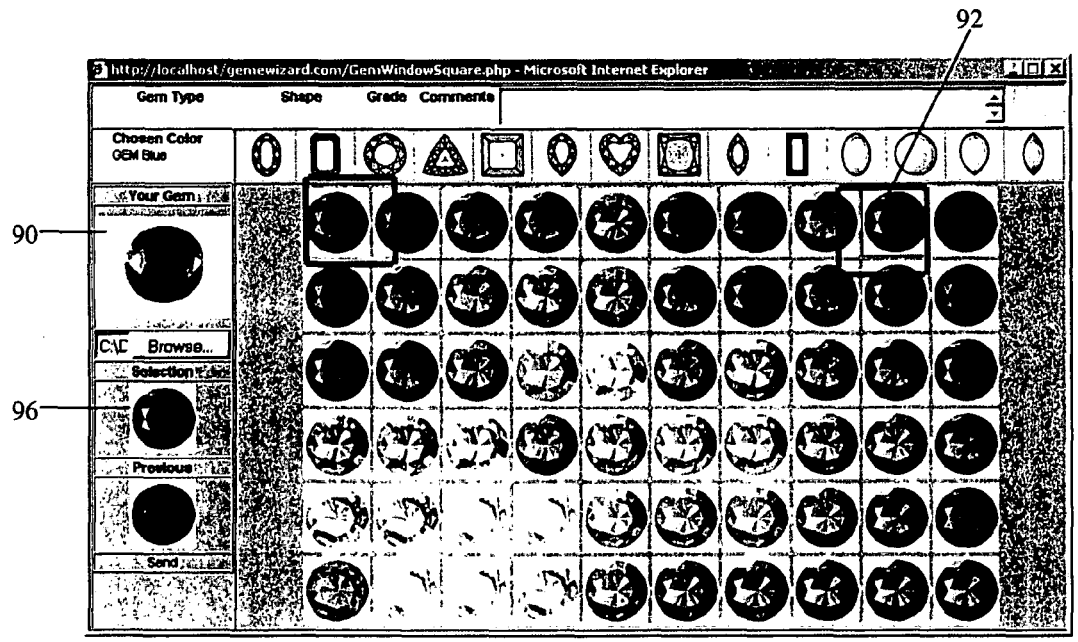
FIG. 9 schematically illustrates the master hues table of FIG. 8 applied to another shape of gem.
Figure 10:
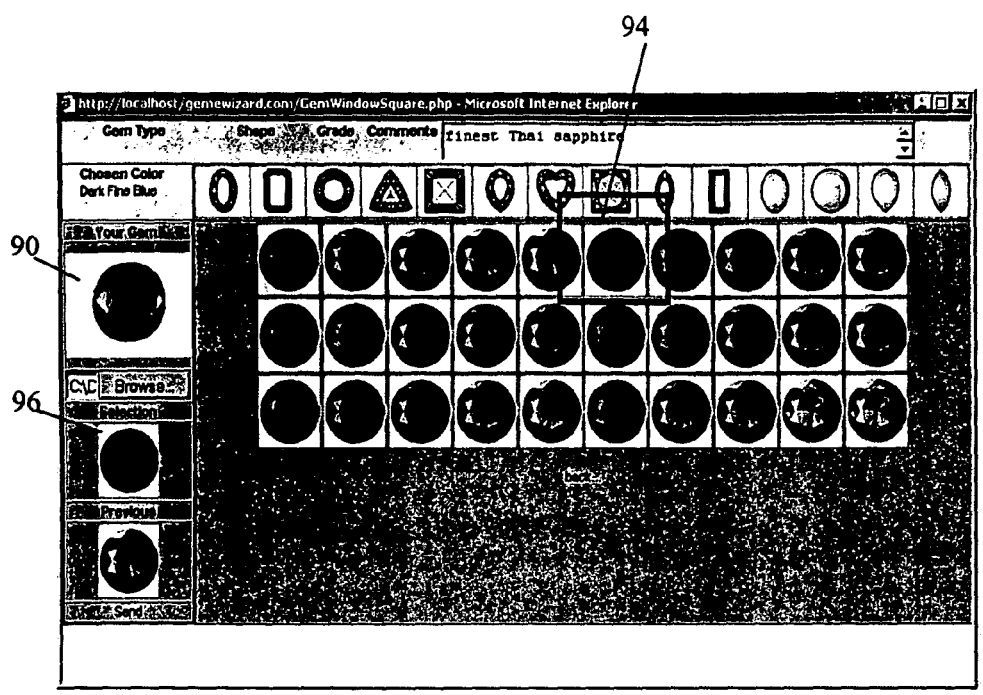
FIG. 10 schematically illustrates a secondary display related to the master-hues table shown in FIG. 9.

This is another way of interactively grading gems. The GemESquare displays all colors available for example in the stock of a certain gem dealer, or are available for a certain type of gem. In FIG. 8 the GemESquare displays 60 master hues for a default of Oval shape. If the Round shape is selected the display will change as shown in FIG. 9. The gem to be graded is displayed in field 90, imported by digital photography or conventional photography and scanning, as known in the art. The nearest hue to the gem in field 90 is the blue in field 92. A double click on this field will open a secondary display shown in FIG. 10, which depicts a selection of 30 "blues". The final choice made by the user is shown in field 94. The selection result in each stage is also copied to field 96 to facilitate the comparison to the target gem in field 90. The final color choice is logged with the target gem, its origin and other details.

It must be noted that in the Gem Mode the name given to a certain hue may differ in different types of gems. Meaning that a certain color for example (26-5-5) may have a "Burma Red" tag name in ruby, but will be tagged "Fine Red" in Rhodolite Garnet. The system obviously includes a large database, which includes the color reference numbers and their relation to a certain type of gem.

The Universal

This powerful grading tool is practically described in reference to FIGS. 2 to 6. Here the interactive "square" method enables the user to match a target gem in field 20 of FIG. 2 with all possible colors available in the spectrum. This tool is useful in gem grading and matching. In order to use this tool the user has to double-click on key 64 in FIG. 7.

The Diamond Mode 68 (FIG. 7)

Figure 11:
FIG. 11 schematically illustrates the main screen of the Diamond Mode, another application included in the embodiment shown in FIG. 7.

This mode is dedicated to the grading of diamonds. The mode start screen is shown in FIG. 11.

The user may select any shape from the shape ruler 100. The colors 102 of diamonds are classified as D to N. These grades were designed by the GIA, and are commonly used by the diamond trade. In this scale D is a colorless diamond while N is slightly yellowish. All the grades in between (E,F, G,H,I,J,K,L,M,N), represent increasing amounts of yellowish tint in the diamond.

These colors are not in the GemESquare, as they are much too pale to be displayed on the screen. However when the user wants to describe a Fancy color (diamond with distinct colors) the user uses the DiamondESquare (optional, not shown), which uses the appropriate terms for common colors used in the trade such as Fancy Yellow, Vivid Pink etc. Note: the Ruler for the shapes (cuts) of diamonds 100 is not the same as for gems 72 (of FIG. 7).

The GIA definition of clarity of diamonds is used by the trade. These are for example: IF, VVS1, VVS2, VS1, VS2, SI1, SI2 and the included grades of 11 to 13 The quality of cut or make (proportions and polish) of the diamond is also an important factor in the pricing of the diamond.

In FIG. 11 the user has searched, for example, for the price of: ½ carat, round, F color, VS2 clarity and was automatically notified in screen field 102 at the price of $ 3200.00 per carat. Below, in screen fields 106 the search in the local stock of the user retrieved 6 items: 19-D to 377-D all being round diamonds, any size F color, VS2 clarity, carrying a GIA certificate with specific prices.

Figures 12, 13:
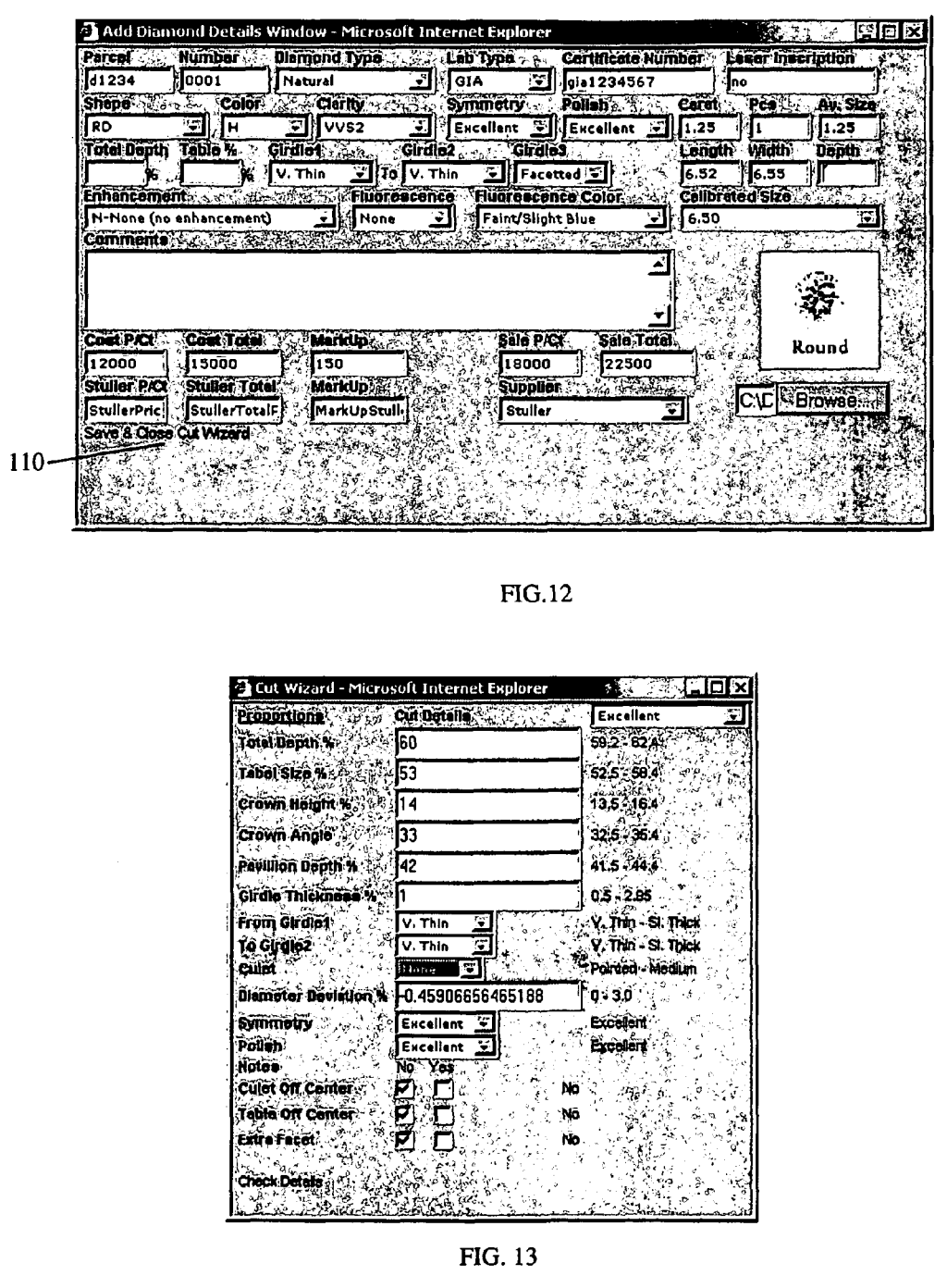

The Diamond Mode includes more expert tools for the professional such as the diamond detail screen shown in FIG. 12. This screen includes a link 110 to the CutWizard tool shown in FIG. 13. The CutWizard, a tool linked to the Diamond Mode or a stand-alone feature, is a computer expert method designed to automatically calculate the quality of make, for example: Regular cut, Excellent cut, Tolkowsky cut, Premium cut, according to established gem trade parameters such as proportions, symmetry and polish. The tolerances accepted for each grade and the "rules" are displayed for comparison.

The Jewelry Mode 66 (FIG. 7)

This mode is dedicated to diamonds and gems mounted in metal (gold, silver) fine structures. Practically, this mode combines most features of the Gem Mode 62 and the Diamond Mode 68.

The Main Advantages of the Invented System and Methods

The system and methods described herein are an "expert-system" with the following main advantages:

1. The method enables the user to define accurately and grade the colors of gems.
2. The method enables users to communicate color, hue tone and saturation, by using a common visual language for the digitally displayed colors of gems of various shapes.
3. The method is fast. It is not time consuming or dependent on transfer of "heavy" photographic data on the internet, but rather involves data stored within one's own personal computer.
4. One's own personal computer acts as a server for most images, grades and pricelists stored on the hard disc.
5. The method includes a vast data of images of digitally produced gems of various shapes and colors, all of which are accurately classified and positioned within known scales of hues, tones and saturations.
6. The hue names and grades correspond to internationally accepted grades by the GIA and the gem trade.
7. The system enables the user to display gems of identical colors in different shapes of cutting at different locations when running the same the program.
8. The system enables the user to keep a record of the grading results (image and data) together with an image of the actual gem.
9. The ability to choose a certain, particularly desired color and search for that particular color gem or search for a gem exactly matching one's own, or create sets of matching gems by searching through the data base of all users and/or suppliers.
10. The ability to compare and study prices of particular colors of gems.
11. Constant grading results over a period of time.
12. Color displayed depending only on the quality of the monitor and the calibration of colors on the particular monitor as known in the art.
13. The system is open to linking and Web upgrades of gem related databases such as: price-lists and inventories of particular suppliers.

From the above, it will be seen that the dataprocessor would be programmed to enable the user to select, from the large number of files (e.g., 19,440 mentioned above) in the database, the image of the selected shape, hue, tone and saturation to be displayed in display field 22 (FIG. 2). It will appreciated, however, that the dataprocessor could be programmed to enable the user to individually select from the database a particular shape, hue, tone and saturation, and to superimpose one over the other in order to build up and to display in display field 22 a composite built-up image.

While the invention has been described with respect to a preferred embodiment, it will be appreciated that this is set forth merely for the purpose of example, and that many other variations, modifications and applications of the invention may be made.

A portion of the disclosure of this patent application document contains material to which a claim for copyright and trademark is made. The copyright and trademark owner has no objection to the facsimile reproduction by any one of the patent document or the patent disclosure, as it will appear in the Patent and Trademark Office patent file or records, but reserves all other copyright and trademark rights whatsoever.

What is claimed is:

1. A method of color grading a particular gem by a user, comprising:
   creating a database in a first data processor that stores digitally created images of different colors of gemstones, said creating further comprising digitally coding gem shapes, hues, tones and saturations from digital photographs of a plurality of gems of different shapes, hues, tones and saturations, the database comprising:
   at least six different shapes of gemstones;
   at least thirty-one different hues for each shape;
   at least six different tones for each hue;
   at least six different saturations for each hue;
   displaying on a screen the at least six different shape images of the gemstones stored in the database;
   selecting by the user a shape from the displayed at least six different shape images best matching, in the user's judgement, the shape of a particular gem to be graded;
   displaying on the screen the at least thirty-one different hue images stored in the database;
   selecting by the user a hue from the displayed at least thirty-one different hue images best matching, in the user's judgment the hue of a particular gem to be graded;
   in response to receiving the user's selection of the hue, displaying on a screen the at least six different tones and the at least six different saturation images stored in the database;
   selecting by the user a tone and saturation from the displayed at least six different tones and the displayed at least six different saturation images best matching, in the user's judgment the tone and saturation of the particular gem to be graded;
   in response to receiving the user's selection of the tone and saturation, generating and displaying on the screen, by the processor, an image of a shape and a color of a gem having the shape, hue, tone, and saturation selected by the user;
   generating and displaying by the processor a code identifying the selected shape, hue, tone and saturation selected by the user, to thereby enable the user to reproduce the generated image of the gem by entering the code into the processor;
   communicating the code to a second data processor for reproducing by the second data processor on a screen associated with the second processor the generated image of the gem having the shape, hue, tone and saturation selected by the user.

2. Apparatus for color grading a particular gem by a user, comprising:
   a database storing digitally created images of different colors of gemstones in different shapes, said images are created by digitally coding gem shapes, hues, tones and saturations from digital photographs of a plurality of gems of different shapes, hues, tones and saturations, the database further comprising:

at least six different shapes of gemstones;
at least thirty-one different hues for each shape;
at least six different tones for each hue; and
at least six different saturations for each hue;
a first data processor programmed to access the database and display the images on a screen for the user for selection;
wherein the first data processor is further programmed to:
display on the screen the at least six different shape images of the gemstones stored in the database;
receive selection from the user of a shape from the displayed at least six different shape images best matching, in the user's judgment the shape of the particular gem being graded;
display on the screen the at least thirty-one different hue images stored in the database;
receive selection from the user of a hue from the displayed at least thirty-one hue images best matching, in the user's judgment, the hue of the particular gem being graded;
in response to receiving the user's selection of the hue, display on the screen the at least six different tones and the at least six different saturation images stored in the database;
receive selection from the user of a tone and saturation from the displayed at least six different tones and at least six different saturation images best matching, in the user's judgment, the tone and saturation of the particular gem being graded;
in response to receiving the user's selection of the tone and saturation, generate and display on the screen an image of a shape and a color of a gem having the shape, hue, tone and saturation selected by the user;
generate and display a code identifying the selected shape, hue, tone and saturation selected by the user, to thereby enable the user to reproduce the generated image of the gem by entering the code into the processor;
communicate the code to a second data processor for reproducing by the second data processor on a screen associated with the second processor the generated image of the gem having the shape, hue, tone and saturation selected by the user.

3. The apparatus according to claim 2, wherein said screen includes a field for displaying a stored image of the particular gem to be graded.

4. The apparatus according to claim 2, wherein said first data processor is programmed to identify the gem shape, hue, tone, and saturation of the image to be displayed in said first-mentioned field, by a string of alphanumeric code elements including a first code element identifying the gem shape, a second code element identifying the hue, a third code element identifying the tone, and a fourth code element identifying the saturation in the image to be displayed in said first mentioned field.

5. The apparatus according to claim 2, wherein said database also includes data relating to price and inventory of gems in stock by a particular gem dealer; and wherein the data processor is programmed to make such data available to the user upon request.

* * * * *